United States Patent [19]
Chee et al.

[11] Patent Number: 5,542,937
[45] Date of Patent: Aug. 6, 1996

[54] MULTILUMEN EXTRUDED CATHETER

[75] Inventors: Hiram Chee, San Carlos; Mark Glowacki, San Jose; Laurent Schaller, Los Altos, all of Calif.

[73] Assignee: Target Therapeutics, Inc., Fremont, Calif.

[21] Appl. No.: 265,708

[22] Filed: Jun. 24, 1994

[51] Int. Cl.$^6$ ............................................. A61M 25/00
[52] U.S. Cl. ............................................. 604/280; 604/264
[58] Field of Search ................................. 604/264, 280

[56] References Cited

U.S. PATENT DOCUMENTS

| | | |
|---|---|---|
| 3,618,614 | 11/1971 | Flynn . |
| 3,752,617 | 8/1973 | Burlis . |
| 4,211,741 | 7/1980 | Ostoich . |
| 4,282,876 | 8/1981 | Flynn . |
| 4,385,635 | 5/1983 | Ruiz . |
| 4,761,129 | 8/1988 | Aste et al. . |
| 4,775,371 | 10/1988 | Mueller, Jr. . |
| 4,888,146 | 12/1989 | Dandenau . |
| 4,899,787 | 2/1990 | Ouchi et al. ............... 138/131 |
| 4,904,431 | 2/1990 | O'Maleki . |
| 4,994,047 | 2/1991 | Walker et al. . |
| 5,085,649 | 2/1992 | Flynn . |
| 5,125,913 | 6/1992 | Quackenbush . |
| 5,183,669 | 2/1993 | Guillemette . |
| 5,258,160 | 11/1993 | Utsumi et al. . |

*Primary Examiner*—Corrine M. McDermott
*Attorney, Agent, or Firm*—Morrison & Foerster

[57] ABSTRACT

This invention is a surgical device. In particular, it is a multilumen catheter having a shaft, at least a portion of which is continuously extruded and undergoes a change in polymer composition during that extension. The invention includes the substituent shaft per se and a method of making the shaft.

22 Claims, 3 Drawing Sheets

MULTILUMEN EXTRUDED CATHETER

FIELD OF THE INVENTION

This invention is a surgical device. In particular, it is a multilumen catheter having a shaft, at least a portion of which is continuously extruded and undergoes a change in polymer composition during that extension. The invention includes the substituent shaft per se and a method of making the shaft.

BACKGROUND OF THE INVENTION

Catheters are used in a variety of procedures to treat vascular maladies throughout the body. Catheters are used to place various treatment materials, drugs, and devices within remote regions of the human body. Catheters with distal balloons are used to treat narrowed regions in the arterial system via percutaneous transdermal angioplasty (PCTA) by expanding the balloon in the region of the plaque narrowing the lumen and pressing that plaque into the vessel wall.

In virtually any of these catheters, the distal end is more flexible than the proximal end and, in the more sophisticated designs, these may be intermediate regions of intermediate flexibility. The construction of these devices has become increasingly more complicated. Catheter construction now often involves multiple layers of tubing, inclusion of braided stiffeners, coil stiffeners and the like. Coaxial inclusion of dissimilar materials such as polyimide tubing has also been the practice. Simplicity has not been the watchword of modern catheter construction. In particular, catheters using distal balloons (such as the PCTA catheter mentioned above) are even more complicated because of the need to include independent tubing with which to fill and to deflate the distal balloon.

U.S. Pat. No. 3,752,617, to Burlis, shows a method and apparatus for producing tubing having different characteristics along its axial length. In general, it shows procedures for making tubing either of a single composition of a mixture of polymers or tubing having coaxially placed inner and outer layers. The patent also suggests methods for changing the physical properties of the tube as it is extruded. In the first variation, there are two extruders, one for homogenizing and delivering a first polymer to a mixing die and a second extruder for homogenizing and delivering a second polymer to the same mixing die. A sequencing control provides, at various time intervals, an increased flow from one of the extruders and a proportionally increased flow from the other extruder. The mixture of the two polymers passes through the die and results in an extruded tubing having varying physical parameters along its axial length.

The second procedure involves a composite extrusion die which produces a tube having sections of exclusively one polymer and other sections of exclusively another polymer with intermediate sections having inner portions of one and outer portions of the other polymer.

U.S. Pat. No. 4,211,741, to Ostoich, also shows a method for extruding laminated medical-surgical tubing. In particular, the tubing is coextruded, multiple-layered medical tubing having a first layer of relatively inexpensive plastic material such as polyvinyl chloride and a second layer of polyurethane. A variation described therein shows the additional extrusion of polyurethane in a third layer onto the two-layer tubing mentioned just above.

U.S. Pat. No. 4,385,635, to Ruiz, shows an angiographic catheter having a soft, flexible, pliable leading tip zone, a main reinforced length, and an intermediate zone between the tip zone and the main length. The main length is made up of a polyamide such as nylon, and the intermediate zone contains a polyamide which is tapered distally and is jacketed by polyurethane. The soft tip is wholly polyurethane. No procedure is given for producing the device disclosed there.

U.S. Pat. No. 4,775,371, to Mueller, Jr., shows a balloon catheter having a multilayered shaft. The shaft may be structured in such a fashion that the various layers taper axially in one fashion or another, typically to permit the distal section to be more flexible than the proximal section. However, rather than being coextruded, the various layers are independently extruded. The outer layer is of a polymer which may be shrunk onto the inner layer after placement on that inner layer.

U.S. Pat. No. 4,904,431, to O'Maleki, shows a method for manufacturing soft-tip catheters having inner rigid polymer layers and soft outer polymer layers. The procedure, however, involves the independent extrusion of the inner sheath with a separate pulling speed so to create depressions or breaks in the inner polymer layer. The inner polymer layer is fed to another extruder having an independently variable pull rate to extrude the softer material onto the outer surface of the inner layer. Wire meshes and the like may be introduced into the device at desired positions.

U.S. Pat. No. 4,994,047, to Walker et al., shows a swellable cannula formed of concentric inner and outer hydrophilic and substantially non-hydrophilic layer structures. A multilumen cannula is shown in FIG. 7 of the patent. The device does not appear to change in flexibility along its axial length. Further, it is not altogether clear what the procedure for creating the device is. The single description (column 9, lines 25–35) appears to suggest that co-extrusion was the procedure.

U.S. Pat. No. 5,085,649, to Flynn, shows a multilayered catheter tubing material. Tubing is shown to have an inner layer of constantly diminishing thickness and an outer layer of constantly increasing thickness, resulting in a catheter body having a consistent diameter along its length. It is said (at column 4, lines 52 and following) that the material is made by discharging from an inner annular orifice of a bi-orifice extrusion head, a first inner resin layer and also discharging from a concentric outer annular orifice of the extruder head an outermost resin layer. The feed rate of the first resin is supplied at a constantly decreasing rate, and the second resin is supplied to the extruder at an increasing rate inversely proportional to the declining rate of the first. The bi-orifice extrusion head is of the type shown in U.S. Pat. No. 4,282,876. No suggestion of multiple lumen material is shown.

U.S. Pat. No. 5,125,913, to Quackenbush, describes a double-layer medical catheter having an integral soft tip made by the co-extrusion of a relatively rigid inner layer and a relatively soft outer layer. The extrusion equipment is operated in such a fashion so to interrupt the supply of the material for the inner, relatively soft layer so to cause a periodic void in the inner wall as the assembly is extruded. The act of interrupting the supply is said to cause a ramp in inner wall thickness at the leading edge of each void. The void is then cut to produce two soft-tipped catheters.

This invention is a continuously extruded, multilumen catheter and catheter body which involves changes in physical parameters—such as flexibility or lubricity—from one end of the body to the other.

SUMMARY OF THE INVENTION

This invention is a surgical device. In particular, it is a multilumen catheter having a shaft, at least a portion of which is continuously extruded and undergoes a change in polymer composition during that extension. The inventive catheter may have discrete sections of different physical parameters or the body may vary in composition so to allow the physical parameters of the shaft to vary slowly rather than in a jump. The catheter body may vary in diameter—both interior and exterior.

DESCRIPTION OF THE INVENTION

As noted above, this invention is a small diameter, multilumen catheter body (and the resulting catheter assembly) which exhibits changes in physical parameters along its length. The catheter body is continuously extended across the changes in physical parameters, typically along its entire length. The invention includes the method of changing the physical parameters during extension.

Figure 1:
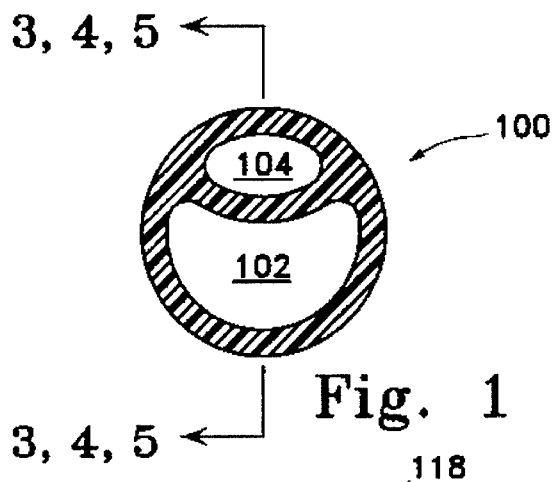
FIGS. 1 and 2 show cross-sectional end views of catheter bodies made according to the invention.
Figure 2:
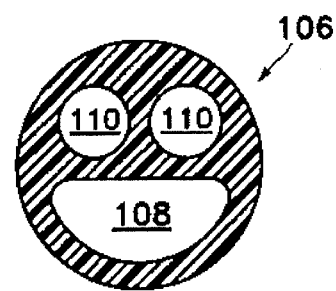

FIGS. 1 and 2 show typical cross sections of the multilumen catheter body. Desirably, the body (100) may contain a major lumen (102) and a minor lumen (104). The two lumens share a common wall. That is to say that the wall surrounding the minor lumen (104) is not completely surrounded by the inner wall of the major lumen (102).

The major lumen (102) may be used for passage of guidewires or treatment drugs or the like and the minor lumen (104) might be used for the passage of a fluid for inflation of a balloon or the like. Of course, the catheter body is not so limited in usage.

The outside diameter of the catheter body desirably is between 0.020" and 0.120"; preferably between 0.026" and 0.065". The diameters of the various lumen may be as small as 0.004".

As is shown in FIG. 2, the cross-section of the catheter body (106) may contain a major lumen (108) and multiple minor lumens (110). Obviously, the catheter body may contain more than three lumens and they may be of any absolute or relative size, but those lumens desirably are within the size ranges specified above.

The materials making up the catheter are typically polymeric and may be either neat or filled. By "filled" we mean that the polymers may contain radiopaque agents such as powdered tantalum or tungsten, barium sulfate, bismuth oxide, bismuth oxychloride, or bismuth carbonate. The term "filled" also includes the use of colorants and reinforcing fibers, etc.

The polymers suitable for the catheter bodies include thermoplastics such as polyethylene, polypropylene, polystyrene, polyurethanes, polyethylene terephthalate, polyesters (such as the Nylons or Hytrel), or polyvinyl chloride. Lubricious polymers such as polyfluorocarbons or polysulfones are also especially preferred. Blends, alloys, copolymers of the noted polymers (such as PEBAX or THV) are also desirable. Especially preferred are polymers which are miscible with other polymers in melt form. For instance, two polyolefins such as LDPE and LLDPE may be used in adjacent sections or layers of the catheter body. They are miscible when melted, will mix with each other to form a homogeneous mixture, and will adhere to each other if merely contacted with each other when in heated or liquid form.

Figure 3:
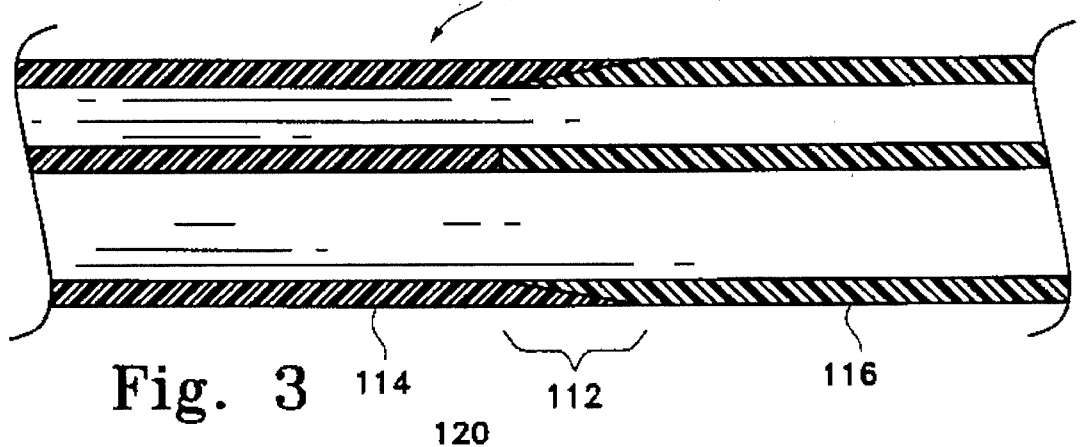
FIGS. 3–5 show fragmentary, cross-sectional side views of joints between sections of catheter bodies made according to the invention.
Figure 4:
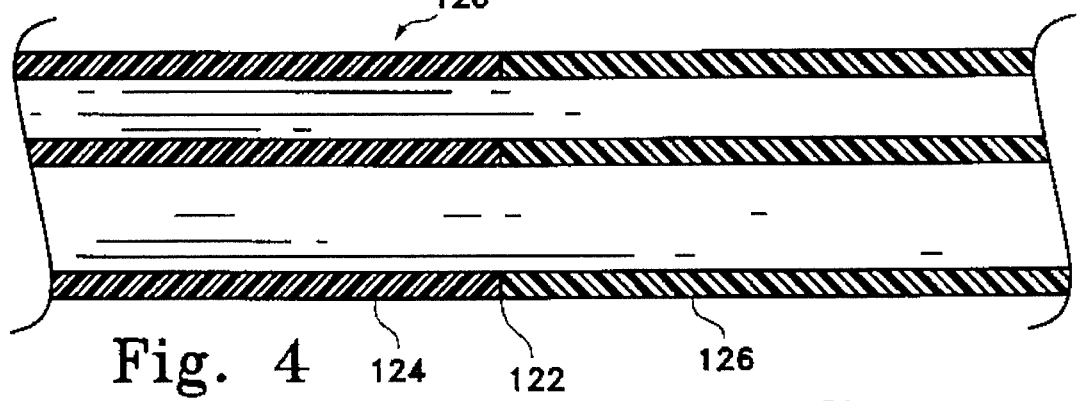
Figure 5:
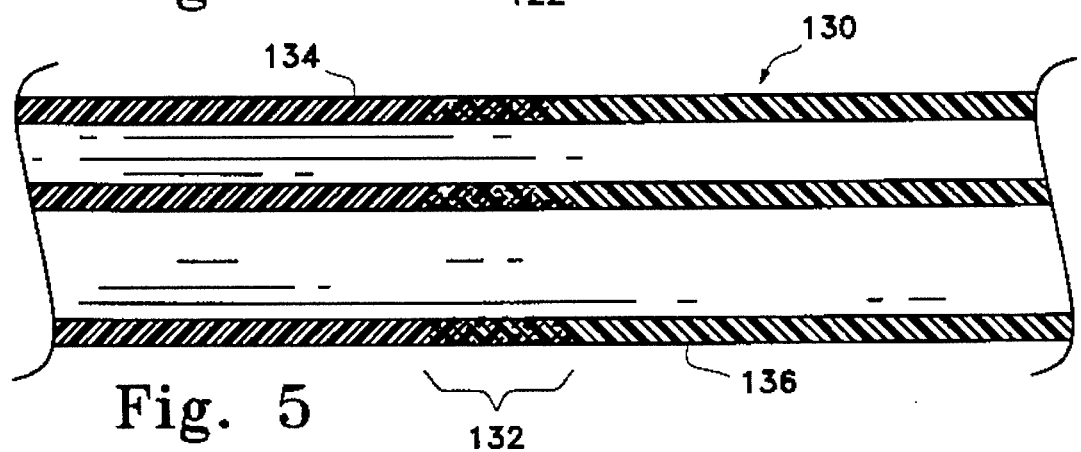

Central to this invention is the concept of changing a physical parameter of the catheter shaft during extension of the shaft. FIGS. 3, 4, and 5 depict, in fragmentary, partial cross-section, side views of the joints which may be found between adjacent sections of the catheter shaft. As will be discussed below, the manner in which the polymers are switched during the extension of the catheter shaft. FIG. 3 shows a cross-section in which the joint (112) is between a first sector (114) of the catheter body (118) and a second sector (116). In this instance, the transition joint (112) varies continuously in physical parameter, e.g., flexibility from one end of the joint to the other.

FIG. 4 shows a variation of the inventive catheter shaft (120) in which the transition joint (122) between the first sector (124) and the second sector (126) is quite abrupt. The junction (123) is similar in structure to a butt joint between two sections of tubing which have been solvent welded together. This joint (122) is more sturdy in that the materials in the adjoining sectors (124 and 126) typically are melt miscible and a small amount of mixing takes place.

FIG. 5 shows a further variation of the catheter shaft (130) in which the transition joint (132) has significant axial length and is a mixture of the materials making up the adjacent sectors (134 and 136). It is within the scope of this invention that the variations shown in FIGS. 3 to 5 may be done in combination.

Certainly, the invention includes catheter bodies in which several sectors are joined by transition joints of the types discussed above. Particularly desirable is a three part catheter in which the distal section is LDPE; the intermediate section is a blend of LDPE and HDPE; and the proximal section is HDPE.

Figure 6:
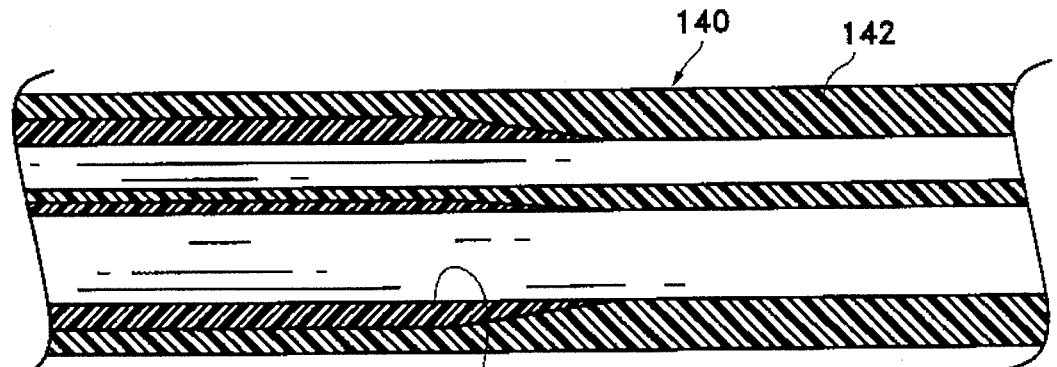
FIG. 6–8 show a fragmentary, cross-sectional side views of a section of a catheter body with a continuous layer along its outer periphery made according to the invention.

FIG. 6 shows still another variation of the inventive catheter body (140) in which the outer layer (142) of polymer is continuous from one end of the depicted section to the other. This would be accomplished by simply ceasing the flow of the polymer making up the inner layer (144) during the co-extrusion procedure. This effect may be had with multiple layers (two or more) of polymers and the number of transitions between different polymers along the axial length of the catheter body.

Figure 7:
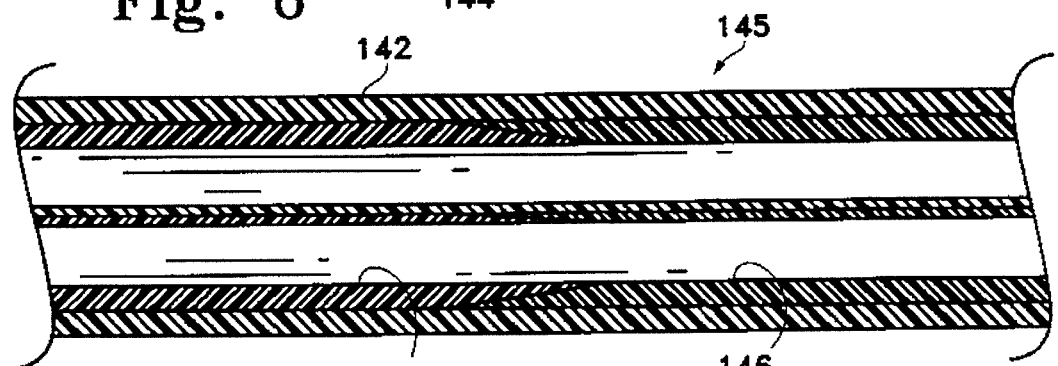

For instance, FIG. 7 shows a variation of the inventive catheter body (145) in which the outer layer (142) of polymer is also continuous from one end of the depicted section to the other. The composition of the inner layer changes form a first polymer layer (146) to a second polymer layer (148).

Figure 8:
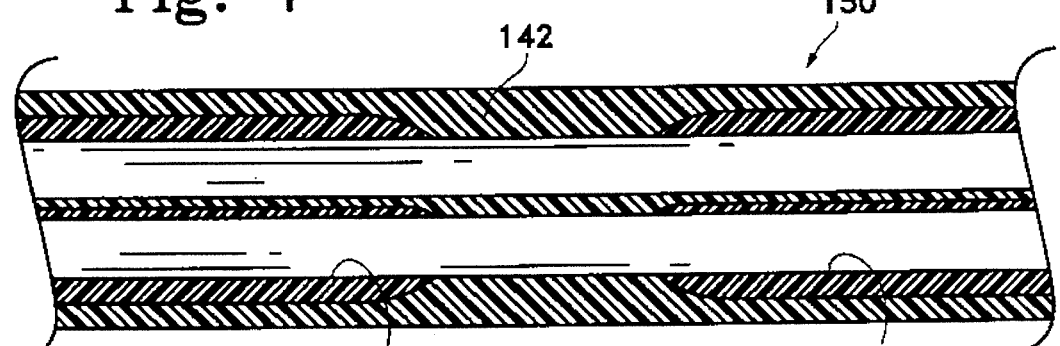

FIG. 8 shows still another variation of the inventive catheter body (150) in which the outer layer (142) of polymer is also continuous from one end of the depicted section to the other. In this variation, the catheter body is extruded in such a way that a first inner layer (152) ceases along the catheter axis, the thickness of the outer polymer expands in the depicted midsection to the total thickness of the catheter wall and an additional polymer layer (154) forms the interior of the third section of the catheter body.

Again, the exterior layer (142) of the catheter bodies shown in the FIGS. 6–8 need not be continuous, but may be varied in composition as are the inner layers shown in those Figures. Additionally, the catheter bodies having the continuous layers shown in FIGS. 6–8 may be combined with the catheter joint configurations shown in the earlier Figures, all as desired by the catheter designer based upon the disclosure herein.

Although the catheter bodies discussed above with relation to FIGS. 1–8 have generally been discussed as straight shaft bodies—that is to say that the outside diameter of the catheter body is approximately constant. However, the invention includes both sections and catheter bodies which do not have constant outside diameters. The "pull rate" and the air pressure applied to the interior of the catheter body during the extrusion process may each be independently adjusted to make the resulting catheter body inner and diameter (independently) either smaller or larger depending upon whether the pull rate and air pressure are increased or decreased.

Figure 9:
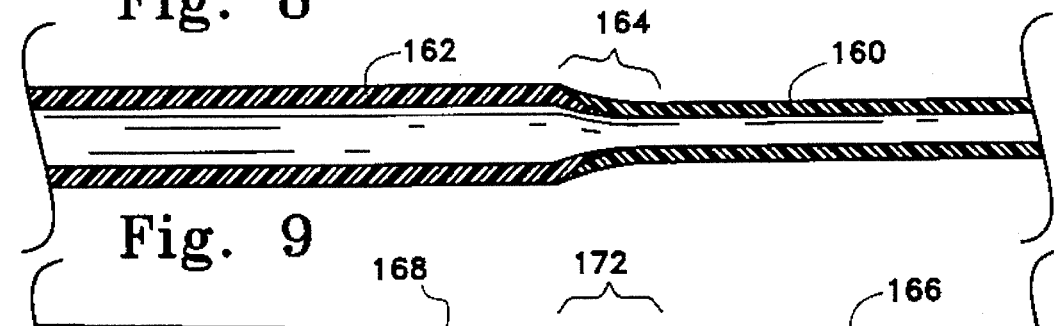
FIGS. 9 and 10 show fragmentary, cross-sectional side views of different catheter sections of the inventive catheter bodies and depict different suitable profiles.

FIG. 9 shows a variation of the invention in which the distal portion (160) has a smaller diameter distal of the transition joint (164) than the diameter with the more proximal portion (162). The joint (164) becomes tapered as well.

Figure 10:
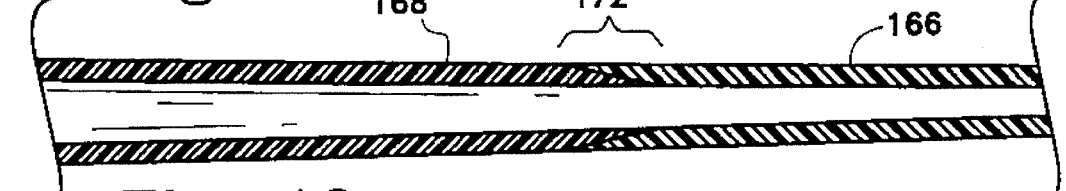

FIG. 10 shows a variation in which the diameter of the distal section (166) and of the proximal section (168) both are tapered about the transition joint (170).

Production of the Catheter Body

Figure 11:
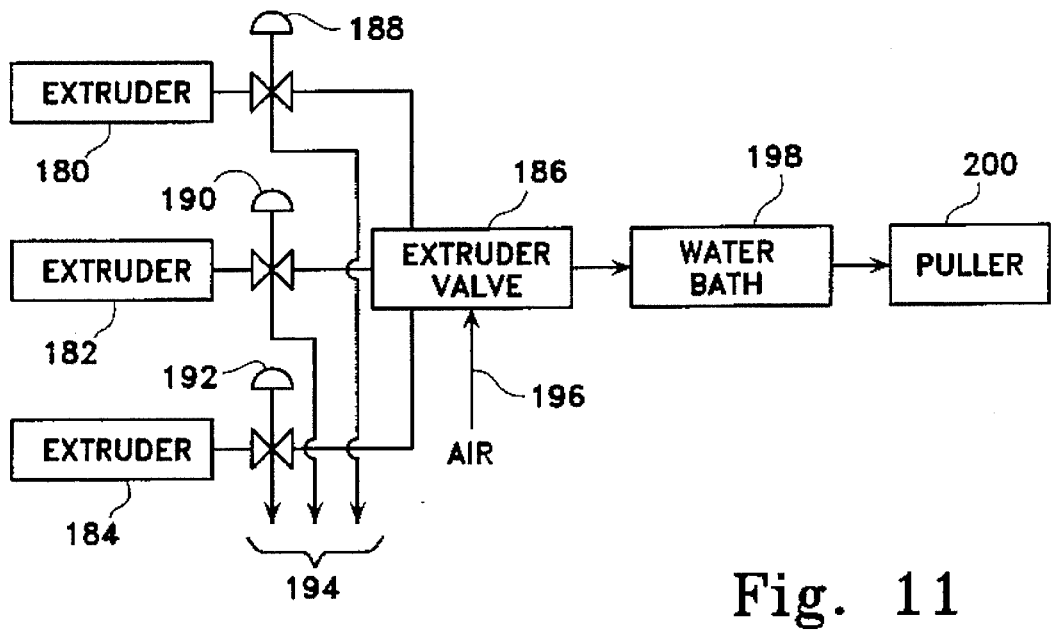
FIG. 11 shows a schematic outline of the extrusion apparatus suitable for creating the catheter.

The catheter body of this invention may be made according to the following procedure. A preferred device for producing these inventive catheters is schematically shown in FIG. 11. In this depiction, three extruders (180, 182, and 184) of typical design and configuration feed a single extruder head or die (186). The extruders may be of known design such as screw extruders and use, for instance, screws typically chosen for the polymers employed in the catheter body. Each of the extruders (180, 182, and 184) have control valves (188, 190, and 192) which can be operated either as proportional valves (partially opening) or as cut-off valves (being only either open or closed). The valves either supply the polymer to the extruder (186) or to a dump region (194), potentially for recycle. Air is supplied to the extruder head (186)—desirably, independently for each catheter lumen extruded.

Figures 12A, 12B:
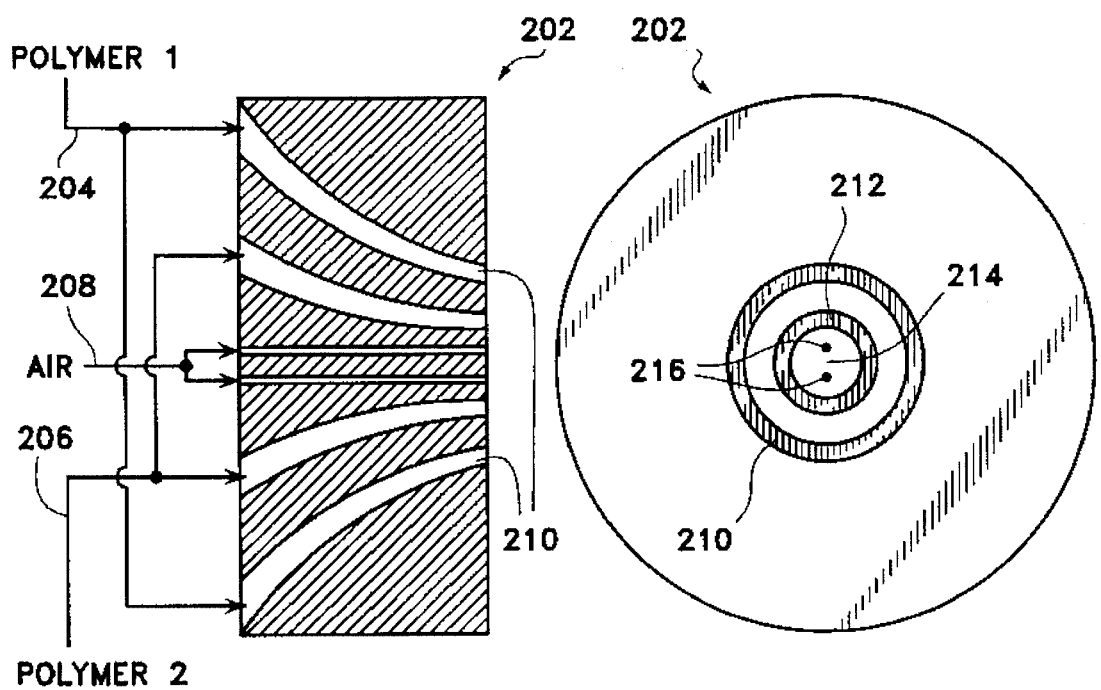
FIGS. 12A and 12B show, respectively, a side cross section of and an end view of an extrusion valve or die suitable for the production of the inventive catheter body.

The polymers from each extruder (180, 182, and 184) enter the extruder head (186), as desired, and exit through the die face, e.g., shown in FIG. 12B. The semi-molten catheter body is then pulled through a water bath (198) typically using a puller (200). The speed of the puller (200) and the pressure of the various extrusion air supplies (196) desirably are variable as needed.

FIG. 12A shows a side view, cross-section of an extrusion die (202) similar in concept to the die (186) in FIG. 11 but capable of handling only two polymer streams simultaneously—although various polymer streams may be mixed or otherwise controlled prior to reaching the die. In this instance, the outer layer of the catheter shaft is formed of a first polymer (204) and the inner layer is formed of a second polymer (206). The first polymer goes through an outer annular region (210) and the second polymer exits through an inner annular region (212) as well as a cross area (214) (shown in FIG. 12B). Two independent air supplies (collectively 208) are shown.

FIG. 12B shows an end view of the extrusion die (202) found in FIG. 12A. Also shown are outer annular region (210), the inner annular region (212), and the crossing area (214) which forms the wall of the lumen defining the additional lumen shown, e.g., FIGS. 1–2. The orifices (collectively 216) for exit of the extrusion air are shown.

The invention has been described by description and by example. The examples are just examples and are not to be used to limit the scope of the invention in any way. Additionally, one having ordinary skill in this art will recognize variations and equivalents without the scope of the appended claims but are considered to be within the spirit of invention as described.

We claim as our invention:

1. A multilumen catheter shaft having a distal end, a proximal end, and a longitudinal axis extending between said distal end and proximal end, said shaft having at least two discrete lumens sharing a common wall between said distal and proximal ends, at least one of said discrete lumens being defined by multiple circumferential layers, at least two of said circumferential layers comprising different polymers, and where the shaft along the longitudinal axis is divided into at least two sectors between those ends having transition regions between said sectors, each said sector having a flexibility normal to the longitudinal axis different from an adjacent sector, where said shaft has been continuously extruded between said distal to said proximal end.

2. The catheter shaft of claim 1 wherein the transition regions between the sectors are shorter in axial length than the sectors and have flexibility which increase distally.

3. The catheter shaft of claim 1 wherein the shaft has a first lumen having a first cross-sectional area and a second lumen having a second cross-sectional area and the first cross-sectional area is relatively larger than the second cross-sectional area.

4. The catheter shaft of claim 1 where the shaft has more than two lumens.

5. The catheter shaft of claim 1 where the transition regions have axial length and comprise mixtures of the materials comprising adjacent sectors.

6. The catheter shaft of claim 1 wherein the sectors comprise polymers selected from the group consisting of polyethylene, polypropylene, polyurethane, polyvinyl chloride, their blends, alloys, and copolymers.

7. The catheter shaft of claim 6 wherein the sectors comprise polymers which are miscible with each other.

8. The catheter shaft of claim 1 in which the shaft has an outer diameter of no greater than 0.120 inches.

9. The catheter shaft of claim 1 in which at least one sector of the shaft comprises wall sections containing multiple layers of different polymers.

10. The catheter shaft of claim 9 in which each sector of the shaft comprises a wall section layer having a single common polymer.

11. A multilumen catheter shaft having a distal end, a proximal end, and a longitudinal axis extending between said distal end and proximal end, said shaft having at least two discrete lumens sharing a common wall between said distal and proximal ends, and where the shaft along the longitudinal axis is divided into at least two sectors between those ends having transition regions between said sectors, each said sector having a flexibility normal to the longitudinal axis different from an adjacent sector, and at least two of said sectors having different outer diameters and comprising at least in part different polymers, where said shaft has been continuously extruded between said distal and said proximal end.

12. The catheter shaft of claim 11 wherein the transition regions between the sectors are shorter in axial length than the sectors and have flexibility which increase distally.

13. The catheter shaft of claim 11 wherein the shaft has three sectors between the distal end and the proximal end.

14. The catheter shaft of claim 13 wherein the transition regions between the sectors are shorter in axial length than the sectors and have flexibility which increases distally.

15. The catheter shaft of claim 11 where the shaft has a first lumen having a first cross-sectional area and a second lumen having a second cross-sectional area and the first cross-sectional area is relatively larger than the second cross-sectional area.

16. The catheter shaft of claim 11 where the shaft has more than two lumens.

17. The catheter shaft of claim 11 where the transition regions have axial length and comprise mixtures of the materials comprising adjacent sectors.

18. The catheter shaft of claim 11 wherein the sectors comprise polymers selected from the group consisting of polyethylene, polypropylene, polyurethane, polyvinyl chloride, their blends, alloys, and co-polymers.

19. The catheter shaft of claim 18 wherein the sector comprise polymers which are miscible with each other.

20. The catheter shaft of claim 11 in which the shaft has an outer diameter no greater than 0.120 inches.

21. The catheter shaft of claim 11 in which at least one sector of the shaft comprises wall sections containing multiple layers of different polymers.

22. The catheter shaft of claim 21 in which each sector of the shaft comprises a wall section layer having a single common polymer.

* * * * *